United States Patent [19]
Fan et al.

[11] Patent Number: 5,182,191
[45] Date of Patent: Jan. 26, 1993

[54] OCCULT BLOOD SAMPLING DEVICE AND ASSAY

[75] Inventors: Eugene Fan, La Jolla; Fon-Chiu M. Chen, San Diego; Michael W. Milner, San Diego; Leslie J. Rehg, San Diego, all of Calif.

[73] Assignee: Pacific Biotech, Inc., San Diego, Calif.

[21] Appl. No.: 409,003

[22] Filed: Sep. 21, 1989

Related U.S. Application Data

[63] Continuation-in-part of Ser. No. 258,036, Oct. 14, 1988, abandoned.

[51] Int. Cl.⁵ .................. G01N 33/535; G01N 33/543
[52] U.S. Cl. ........................................ 435/7.9; 422/56;
422/57; 422/58; 422/61; 435/7.92; 435/805;
435/810; 436/66; 436/518; 436/808; 436/810;
128/638; 128/749; 128/759
[58] Field of Search .................. 435/28, 810, 88, 805,
435/7.92, 970; 436/66, 904, 810, 808, 518;
422/56, 57, 59, 61, 58; 128/638, 759, 749;
206/204, 472, 423, 569

[56] References Cited

U.S. PATENT DOCUMENTS

| | | | |
|---|---|---|---|
| 3,917,452 | 11/1975 | Rittersdorf et al. | 260/240 |
| 3,986,833 | 10/1976 | Mast et al. | 252/408 |
| 4,035,150 | 7/1977 | Jaffe | 210/357 |
| 4,063,894 | 12/1977 | Ogawa et al. | 23/230 B |
| 4,148,611 | 8/1979 | Nand et al. | 23/230 B |
| 4,219,336 | 8/1980 | Guthlein et al. | 23/230 B |
| 4,225,557 | 9/1980 | Hartl et al. | 422/56 |
| 4,259,964 | 8/1981 | Levine | 128/638 |
| 4,260,393 | 8/1981 | Gibson | 23/230 B |
| 4,273,741 | 6/1981 | Levine | 422/56 |
| 4,277,250 | 7/1981 | Melnick et al. | 23/230 B |
| 4,329,317 | 5/1982 | Detweiler et al. | 422/58 |
| 4,333,734 | 6/1982 | Fleisher | 23/230 B |
| 4,365,970 | 12/1982 | Lawrence et al. | 436/66 |
| 4,367,750 | 1/1983 | Levine | 128/638 |
| 4,372,746 | 2/1983 | Habenstein | 436/66 |
| 4,378,971 | 4/1983 | Schwartz | 436/66 |
| 4,382,064 | 5/1983 | Detweiler et al. | 422/58 |
| 4,386,053 | 5/1983 | Motobayashi | 422/56 |
| 4,420,353 | 12/1983 | Levine | 156/227 |
| 4,473,079 | 9/1984 | Jasper et al. | 436/66 |
| 4,486,536 | 12/1984 | Baker et al. | 436/66 |
| 4,492,124 | 1/1985 | Fleisher et al. | 73/864.44 |
| 4,493,892 | 1/1985 | Fleisher | 435/28 |
| 4,521,520 | 6/1985 | Jacke | 436/66 |
| 4,526,869 | 7/1985 | Schwartz | 436/66 |
| 4,539,180 | 9/1985 | Schwartz | 422/58 |
| 4,541,987 | 9/1985 | Guadagno | 422/56 |
| 4,543,338 | 9/1985 | Chen | 436/170 |
| 4,559,949 | 12/1985 | Levine | 436/66 |
| 4,562,043 | 12/1985 | Mennen et al. | 436/66 |
| 4,567,148 | 1/1986 | Schwartz | 436/66 |
| 4,578,358 | 3/1986 | Oksman et al. | 436/66 |
| 4,578,359 | 3/1986 | Oksman et al. | 436/66 |
| 4,615,982 | 10/1986 | Lawrence | 436/66 |
| 4,645,743 | 2/1987 | Baker et al. | 436/66 |
| 4,672,029 | 6/1987 | Washburn et al. | 435/10 |
| 4,673,654 | 6/1987 | Talmage | 436/66 |
| 4,675,160 | 6/1987 | Talmage et al. | 436/66 |
| 4,676,950 | 6/1987 | Foster | 422/56 |
| 4,683,197 | 7/1987 | Gallati | 436/66 |
| 4,708,765 | 11/1987 | Newman et al. | 156/655 |
| 4,719,181 | 1/1988 | Schobel et al. | 436/66 |
| 4,725,553 | 2/1988 | Guadagno | 436/66 |
| 4,789,629 | 12/1988 | Baker et al. | 435/28 |

Primary Examiner—Robert J. Hill, Jr.
Assistant Examiner—Christopher L. Chin
Attorney, Agent, or Firm—Knobbe, Martens, Olson & Bear

[57] ABSTRACT

The invention provides a disposable device for collecting, transporting and storing semi-solid or liquid specimens prior to analysis. A sample of the collected specimen is removed from the device for analysis by means of a detachable transferring stick, one area of which is the sample collecting portion of the device and another area of which is an integral handle. The device also provides for the collection of a liquid sample drained from a defined volume of a semi-solid specimen through porous screen and collected on the detachable transferring stick. A sample of the specimen or liquid from it may be flushed from the stick for a qualitative or quantitative determination of analyte. The device is useful in collecting fecal specimens and detecting occult blood therein by a determination of hemoglobin in the specimen itself or in a liquid sample drained therefrom.

29 Claims, 2 Drawing Sheets

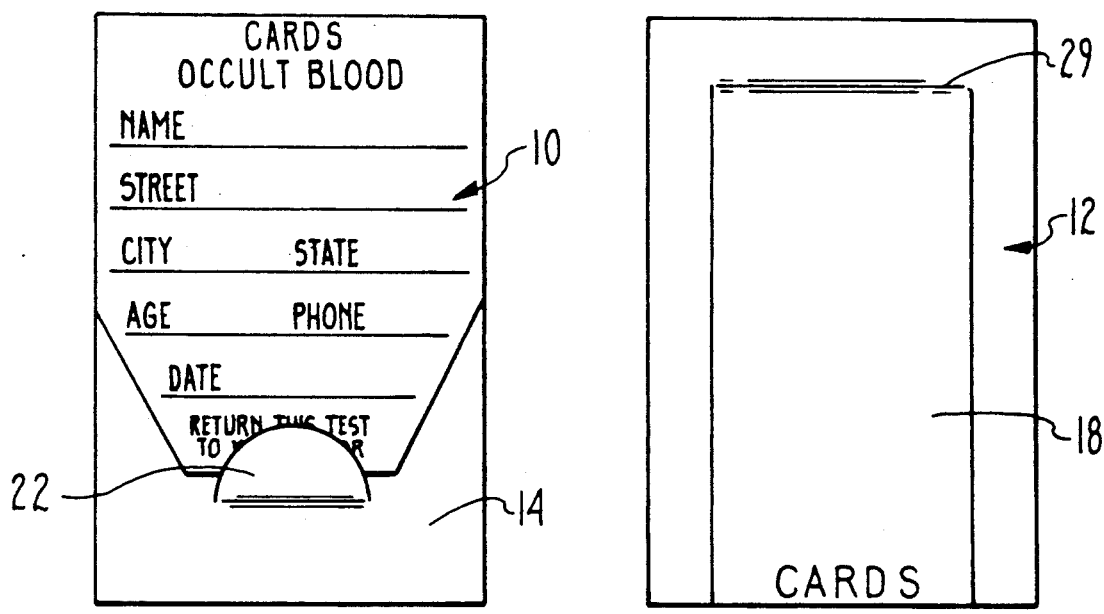
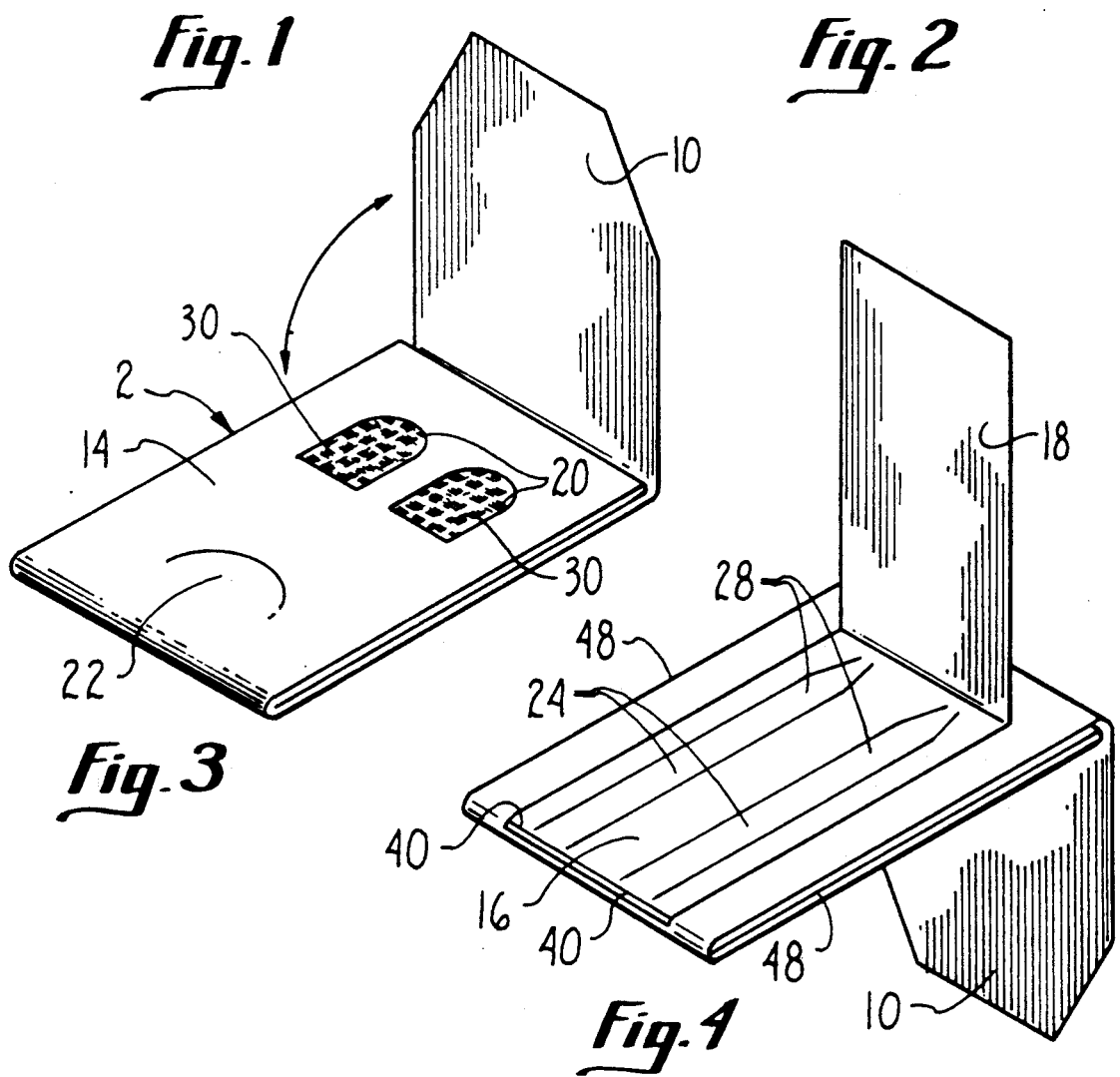

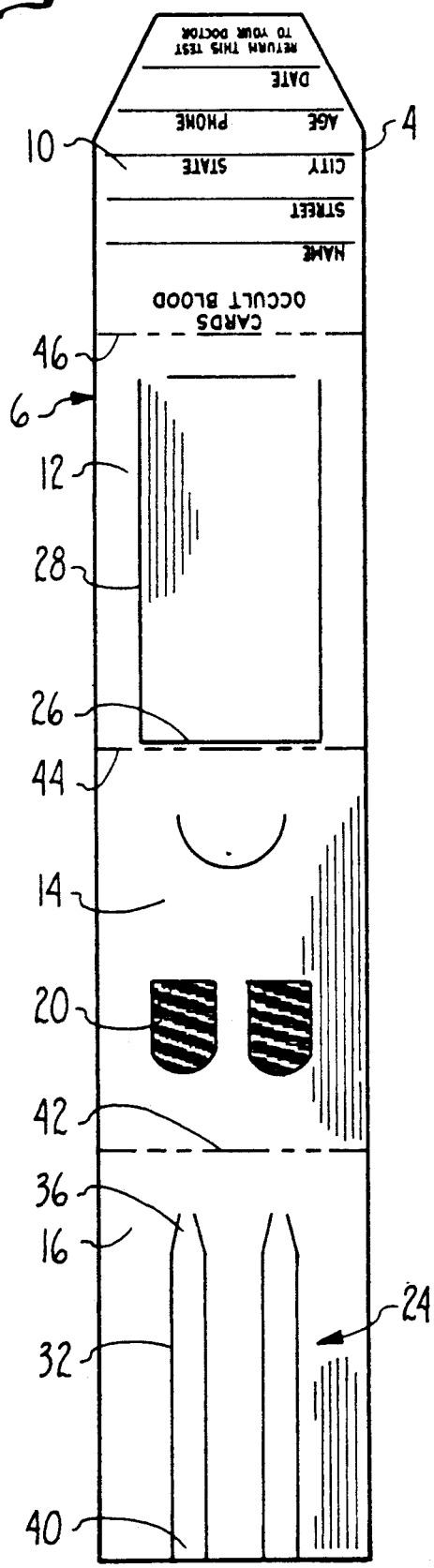
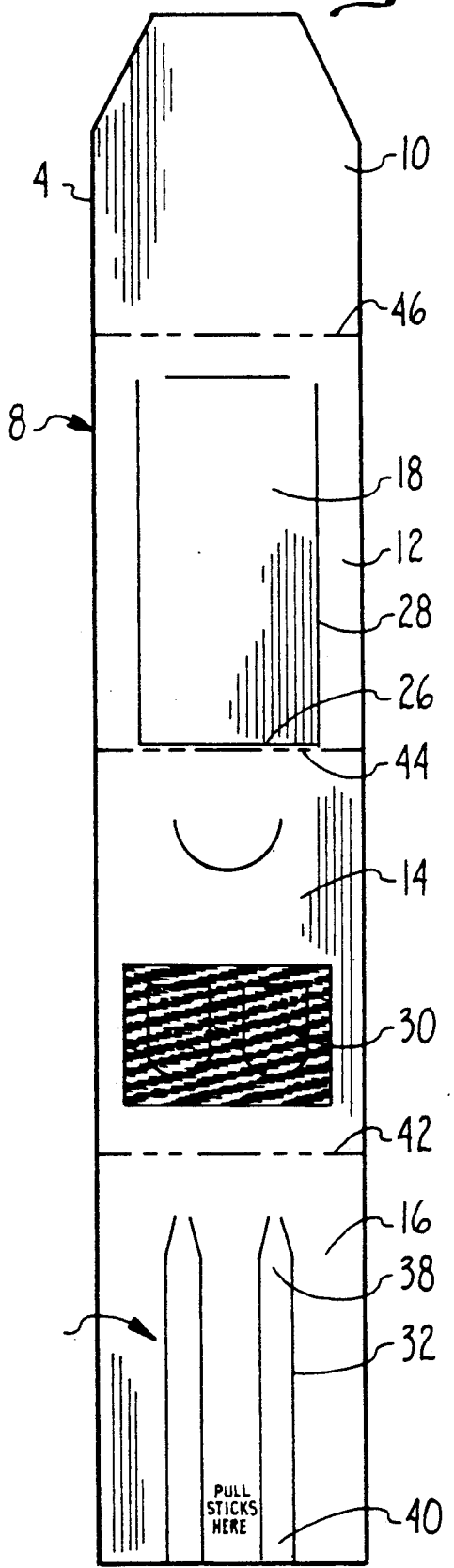

OCCULT BLOOD SAMPLING DEVICE AND ASSAY

RELATION TO RELATED APPLICATION

This application is a continuation-in-part of U.S. application Ser. No. 258,036, filed Oct. 14, 1988, now abandoned.

BACKGROUND OF THE INVENTION

The present invention relates to disposable devices for the collection, transport, and storage of a specimen prior to analysis for a component thereof, and specifically to an integral feature which provides for convenient removal of a sample of the collected specimen. The present invention also relates to assays for soluble components in colored or opaque semi-solid specimens, and specifically to a method for obtaining a liquid sample from such specimens.

The collection, transportation and storage of many types of specimens for delayed routine analysis requires appropriate and efficient packaging systems. Packages for specimens of potentially infectious clinical biological materials sent through the mails should be lightweight, sealable, unbreakable, and disposable. Further, removing samples from the packaged specimens must be accomplished with as little handling as possible to avoid contamination.

Further, the chemical detection of soluble components in the liquid phase of semi-solid specimens can be difficult if the liquid phase is not first isolated. Common qualitative colorimetric tests cannot be used because a positive test result can be obscured by the opaque, colored material of the specimen. At the same time, however, conventional isolation procedures are impractical in the case of routine medical tests which must be processed economically. Therefore special methods have been developed to analyze these specimens intact, without first extracting a liquid sample.

Specimens of fecal material are commonly collected and mailed to a commercial laboratory for analysis for occult blood. This type of specimen is a paradigm of the specimen collecting and analysis difficulties indicated. A number of fecal occult blood test systems use disposable, sealable collecting devices suitable for storage and transport of a fecal specimen preliminary to the analysis for hemoglobin. These tests usually incorporate a reagent for the guaiac test, capable of detecting hemoglobin in an intact fecal specimen. Guaiac chemistry is based on the ability of hemoglobin present in blood to act as a peroxidase, releasing $O_2$ from peroxide to change the color of an indicating guaiacum resin to a blue color.

U.S. Pat. No. 4,225,557 to Hartl discloses a typical physical design for an occult blood test, which provides an area having an absorbent surface and impregnated with guaiac, mounted within a frame on a rigid panel of a folder, onto which a fecal specimen is applied. After the specimen is collected, a flap of the folder covers the absorbent surface and seals. At this point, the system is stable, and the device may be taken or mailed to a laboratory, where the test for hemoglobin is performed. To test for the presence of hemoglobin, a few drops of hydrogen peroxide are applied to the exposed underside of the absorbent layer. The peroxide passes through to react with any hemoglobin present in the specimen, and in a positive test, the guaiac in the absorbent layer is converted to a blue color. The color is conveniently observed, free of interference by the opaque, colored specimen, on the same underside of the absorbent layer.

This form of the test has a number of defects and they have been met by a series of modifications and improvements. First, guaiac is easily oxidized to a blue color on prolonged exposure to air. Therefore, it must be protected from oxidation in order to prevent incorrect results, and its effectiveness verified at the time the assays are performed. U.S. Pat. No. 4,382,064 to Detwiler et al. discloses a coating for surfaces in contact with guaiac in the device, the coating comprising the antioxidant BHT incorporated into a varnish applied to the surfaces. U.S. Pat. No. 4,365,970 to Laurence et al. discloses on-slide positive and negative performance monitors for the guaiac test wherein the positive control comprises a hemoglobin component.

Another defect in the guaiac test for occult blood is that it is subject to interference from other oxidative reactions in the specimen which give rise to false positive results. One source is that of peroxidases present in foods which apparently survive the digestive process and remain active in fecal material. U.S. Pat. No. 4,333,734 to Fleischer discloses an improved guaiac chemistry which comprises inhibitors of competing peroxidases. Another is that of oxidizing agents used to clean toilet bowls from which the specimens are usually retrieved, and U.S. Pat. No. 4,675,160 to Talmage et al. discloses test controls to detect this source of interference.

Another problem is that these tests do not provide for reproducible sampling. For even qualitative tests to be reliable and significant from test to test, they should be carried out on a defined, preferably constant, specimen volume. U.S. Pat. No. 4,273,741 to Levine discloses a constant volume stool testing device wherein the specimen is applied to a surface containing an area which is a recessed grid. That portion of specimen remaining above the grid is removed before the test is performed.

The consequences of a false positive occult blood test, indicating colo-rectal bleeding, are serious since it requires the consideration of more serious invasive diagnostic procedures. For this reason, it is customary to confirm a positive occult blood test with a more specific test for hemoglobin. To verify the test results independently, for example, by immunoassay for hemoglobin, it is often necessary to secure a sample of the fluid phase of the specimen, substantially uncontaminated by solid material.

One occult blood testing device provides for a guaiac test for hemoglobin together with simultaneous sampling of a liquid filtrate of the fecal specimen. U.S. Pat. No. 4,645,743 to Baker discloses a fecal testing device comprising an absorbent specimen pad having a pocket in which is inserted a second liquid sampling sheet. The specimen pad can be inserted and mounted in a rigid frame which comprises a sample receiving sheet impregnated with guaiac. After a fecal specimen is deposited on the absorbent pad, it is placed, specimen side down, in the frame against the receiving sheet. The guaiac test is performed in the conventional way, by applying a few drops of peroxide on the underside of the receiving sheet. The second sampling layer, the insert, receives a liquid portion of the fecal specimen which has filtered inwardly from the absorbent pad. The insert, containing the liquid sample, can be removed and cut into portions from which the retained liquid can be eluted and assayed by any desired procedure, for example, a radioimmunoassay.

Methods similar to the Baker device for follow-up or supplementary testing are unsatisfactory in a number of ways, and can lead to incorrect results.

First, a liquid sample which has been filtered through a volume of an absorbent pad may be less concentrated and its composition not representative of the original liquid sample. Absorbent material exerts an initial chromatographic effect on the solutions passing through it, retarding the passage of large molecules with respect to smaller molecules, particularly those of water. Unless the total volume of the liquid in the specimen is sufficient to saturate the pad and thus overcome this effect, the filtered liquid sample will be diluted and its relative composition distorted by the extraction of larger molecules. The liquid content which will flow from most semi-solid biological specimens is usually quite limited. The effect of collecting a small volume of filtered liquid therefrom through an absorbent pad in almost all cases will be to reduce the sensitivity of any subsequent test, especially with respect to the large molecules.

Further, unless the liquid sample collected on the receiving surface is drained from a defined sample volume and collected in a defined area, the results of a subsequent assay are unreferenced and cannot be compared over a period of time or from subject to subject. Again, the sensitivity of testing cannot be defined.

There are other difficulties in attempting to collect a liquid sample from a fecal specimen in conjunction with a guaiac test. In the use of devices such as that of Baker, the portion of the insert containing the liquid sample must be cut or punched from the insert, a process which requires unsanitary contact.

Another major problem with such devices is that they must sit for a substantial period of time before they are analyzed. Often, this involves transit through the mails, under a wide variety of ambient conditions of temperature and humidity. Sticking together of parts of the collection device is a major problem, as is drying and possible loss of portions of the specimen.

Such collections also risk the contamination of the liquid sample with wet guaiac indicator diffusing from the specimen receiving sheet. In addition, the device as disclosed and similar devices are complex and expensive to fabricate.

Immunological tests for hemoglobin are presently available in rapid, convenient, easily interpretable colorimetric form equivalent or superior in sensitivity to the guaiac test. Further, solid-phase immunoassays can concentrate analyte from dilute samples, thus achieving higher sensitivity than colorimetric chemistries. Such tests may be substituted for the guaiac test as a primary rather than confirmatory procedure if there is a means provided to obtain an appropriate liquid or semi-liquid sample from the fecal specimen. Also, in an immunological test for occult blood, just as in the guaiac test, a time lapse between the collection of the specimen and the hemoglobin assay does not affect the accuracy of the result. Accordingly, the design of a fecal specimen collecting device for occult blood testing directed only to the collection of an appropriate liquid fraction can be freed from the requirements and restrictions of the guaiac chemistry.

Devices which can collect fecal specimens for analysis without commitment to a defined chemistry can also be used to collect any semi-solid specimen in an analogous way. Such specimens can be blood clots, vomitus, sputum, pus, or solid tissue. The collected material can then be conveniently eluted and analyzed for a variety of substances according to appropriate analytical procedures, rather than restricted to an in situ colorimetric chemical analysis.

It is therefore an object of the invention to provide a device capable of collecting a liquid or semi-solid specimen and providing for convenient sampling therefrom.

Another object is to provide a convenient, sanitary, folding sample device that can be shipped through the mail or stored for a period of time with greatly reduced drying and sticking problems.

It is further an object of the invention to provide a device capable of collecting a sample of liquid from a semi-solid specimen wherein the sample accurately represents the native composition of the liquid.

It is also an object of the invention to provide a device capable of collecting a representative sample from a defined volume of the specimen.

It is further an object of the invention to provide a device which allows for the sanitary and convenient removal of a sample of the thus-collected specimens to a separate test device.

It is further an object of the invention to provide a procedure whereby a sample collected from a fecal specimen in the device of the invention is then analyzed for hemoglobin by a solid-phase enzyme immunoassay, and this procedure is a screening test for occult blood.

It is further an object of the invention to provide a device capable of conveniently collecting a representative sample from a liquid or semi-solid specimen, which device can be easily and inexpensively fabricated from a unitary blank.

SUMMARY OF THE INVENTION

The device of the present invention provides a means to collect a sample of a semi-solid specimen, a liquid or a sample of the liquid component of a semi-solid specimen. Preferably, the specimen is a biological specimen. The device also provides a means to remove the collected sample from the device by means of an integral detachable transferring stick. The detachable strip has an integral handle which is used to remove it, together with the collected sample, from the device.

A collected sample is eluted from the detachable strip by a volume of solvent, and samples of this volume can then be analyzed, both by qualitative and quantitative means.

According to one aspect of the invention there is provided a system for use in the collection of a sample used in the analysis of a liquid or semi-solid specimen, comprising a sampling folder having a front panel, a back panel, and a specimen receiving portion covered by the front panel, the two panels being in overlying relationship to one another, and the front panel being openable to permit application of a specimen to the specimen receiving portion. An area of this specimen receiving portion comprises material onto which a specimen can be applied, and which is capable of retaining the specimen. In a preferred embodiment, the specimen is a biological specimen. The specimen receiving portion comprises, at least in part, a detachable sample transferring stick having a handle portion and a sample collecting portion. In one embodiment, the sample transferring stick is a part of the back panel. In another embodiment, the sample transferring stick is attached to the inside of the back panel. According to another embodiment of this aspect of the invention, a central leaflet between the front and back panels comprises the specimen receiving portion. In this embodiment, the sample transferring stick may comprise a part of the central leaflet. In another embodiment, the transferring stick is attached to the back of the central leaflet. In a particularly preferred embodiment, the central leaflet is a bilayer of two panels, wherein one of the panels comprises the specimen receiving portion and the other comprises the sample collecting portion.

The specimen receiving portion of the sampling device may comprise, at least in part, a sheet of porous material, in front of the specimen application area to which the specimen can be applied, wherein the porous material is adapted to permit only a portion of the specimen to be transferred through the porous material onto the specimen receiving portion. In one embodiment of the invention, wherein the specimen is generally opaque, the specimen application area includes indicia thereupon which remain visible only when a predetermined amount of specimen of less than that amount has been applied thereto so that a user can determine that the amount of specimen applied does not exceed the predetermined amount.

In a particularly advantageous embodiment, the specimen receiving portion is porous material that has been coated with a release agent to prevent sticking of the specimen to the porous material and to prevent sticking together of the various layers of the sampling device.

In yet another embodiment of the invention, the back panel includes a means for providing a opening through which the sample transferring stick can be removed.

In a particularly preferred embodiment, the panels and the stick of the invention are formed from cellulosic material. The sample collecting portion of the transferring stick may also have an additional layer of absorbent material thereon.

According to another aspect of the invention, there is provided a sampling device as part of a kit which further comprises a mixing cup; a liquid for use in the mixing cup to extract the sample from said sample collecting portion; and a assay device for determining the presence or quantity of an analyte in the extracted sample. In a preferred embodiment, the specimen is a stool sample and the analyte is hemoglobin. In yet another embodiment of this aspect of the invention, the assay device in form of a kit includes a receptacle for holding the cup. The cup may be built into the device. According to yet another aspect of the invention, there is provided a method for collecting and analyzing a specimen comprising the steps of opening the front panel of the sampling folder; applying a specimen to the specimen application area of the specimen receiving portion; closing the front panel; and thereafter removing the sample transferring stick by grasping only the handle portion thereof, so that contact between a user and a sample is avoided during the sample removing step; and analyzing the sample on the sample collecting portion of the removed stick for the presence of an analyte. In a preferred embodiment, the specimen is a stool specimen and the analyte is hemoglobin. In a particularly preferred embodiment, the analyzing step comprises an immunoassay. In a particularly preferred embodiment the sampling device in the context of a kit is a sampling device in which the specimen receiving portion comprises at least in part a sheet of coated or non-coated porous material in front of a specimen application area to which the specimen can be applied, wherein the porous material is adapted to permit only a predetermined amount of the specimen to be transferred to the porous material onto said specimen receiving portion. The coating material is preferably a release agent that prevents dried sample from sticking to the porous material in preference to the specimen receiving portion.

BRIEF DESCRIPTION OF THE DRAWINGS

FIG. 1 is a front view of a preferred embodiment of the folded sampling device.

FIG. 2 is a back view of the folded sampling device.

FIG. 3 is a perspective view of the sampling device with the front cover lifted, exposing the exterior surface of the specimen application panel.

FIG. 4 is a perspective view of the sampling device with the openable flap of the back end lifted, exposing the exterior surface of the liquid sample collecting panel.

FIG. 5 is a planar view of the face surface of the unitary blank from which the sampling device is folded.

FIG. 6 is a planar view of the reverse surface of the unitary blank from which the sampling device is folded.

DETAILED DESCRIPTION OF THE INVENTION

The sampling device 2, according to a preferred embodiment illustrated in FIGS. 1 through 6, contains a sampling bilayer 48 enclosed as a central leaflet between a front panel 10 and a back panel 12. The sampling bilayer 48 consists of a specimen receiving panel 14 and a sample collecting panel 16. The front surface of the folded sampling device 2, as best seen in FIG. 1, is made up of the front panel 10 which is folded down over the exterior surface of the specimen receiving panel 14. The front cover 10 is held in place by the insertion of its lower edge into a semi-circular slit 22 cut into the specimen receiving panel 14.

The front panel 10 has on its face surface 6 printed matter which may include titles and trademark, and indicated areas for recording information. The back surface of the folded sampling device 2, as best seen in FIG. 2, is the back panel 12. The back panel 12 has an openable flap 18 which is defined by an open slit 26, perforated side edges 28 and a fold line 29 in the area proximal to the back panel 12.

In the folded sampling device 2, the specimen receiving panel 14 and the sample collecting panel 16, lie with their reverse surfaces 8 together to form a bilayer central leaflet 48.

The specimen receiving panel 14, as best seen in FIG. 3, is exposed by lifting the front panel 10. The specimen receiving panel 14, in addition to the semi-circular slit 22 has a pair of punched-out open specimen application areas 20 located in the upper half of the panel. The punched-out open specimen application areas 20 are filled by a porous screen 30 attached to the reverse surface 8 as best seen in FIG. 6.

The sample collecting panel 16, as best seen in FIG. 4, is exposed by lifting the openable flap 18 of the back panel 12. The sample collecting panel 16 comprises a pair of detachable sample transferring sticks 24 having a tip 36, a sample collecting area 38, and an integral handle 40. The sample sticks 24 are defined by perforated or notched edges 32. Porous screen 30 may also be coated, to reduce the likelihood that the screen 30 will adhere to sample sticks 24, especially in sample collecting area 38, when samples are collected or transferred.

The device may alternatively comprise a monolayer central leaflet consisting of the specimen receiving panel 14 enclosed between the front 10 and back 12 panels. In this embodiment, the back panel 12 also serves as the sample collecting panel 16 and the transferring sticks 24 are integral parts thereof. In another embodiment of this type, the back panel 12 may be a solid sheet and the transferring sticks 24 are attached to the interior side thereof so as to underlay the open sample application areas 20 of the specimen receiving panel 14. Alternatively, the central leaflet may comprise the transferring sticks.

The sampling device 2 may be used to collect a sample of a liquid or semi-solid specimen in either a defined or undefined volume. A defined volume of a liquid or semi-solid specimen may be collected, or a liquid sample may be taken from a collected semi-solid specimen.

The open specimen areas 20 provide for sampling a specimen of a defined volume. A defined specimen application area is defined by the geometry of the open specimen areas 20. The specimen volume may be defined by filling an open specimen area 20 with a semi-solid specimen to the depth of the porous screen 30. The porous screen 30 preferably is one with large openings; that is a screen with a coarse mesh.

The specimen volume which is then retained in the screen and predetermined by the size of the openings and the depth of the porous screen 30 may in this way be transferred through the porous material and onto the specimen receiving portion.

The sampling device 2 may also be used to collect a defined sample volume of semi-solid specimen according to constructions that eliminate the filter screen 30. For example, the specimen receiving area 14 (which may be identically the sample collecting area 16) may be imprinted with graphic symbols or other indicia which become obscured when an adequate amount of an opaque specimen is applied.

A defined volume of a liquid specimen can be sampled by providing an area of defined absorbency, for example in the open specimen applications areas 20, or on the sample collecting portion 16 of the device 2 and applying the specimen thereto.

The device also provides for obtaining a liquid sample from a defined volume of a semi-solid specimen. A liquid sample taken from a semi-solid specimen may be used for either a qualitative analysis for the presence of components or a quantitative analysis for the concentration of components. A liquid sample for qualitative analysis may be collected from a relatively small semi-solid specimen through an absorbent filter on the specimen receiving surface or onto an absorbent layer on the sample collecting surface. If the amount of fluid sample that passes through an absorbent filter is large enough to overcome chromatographic effects which alter the concentration of its components, the liquid sample may be analyzed quantitatively. A liquid sample for quantitative analysis may be collected from even a relatively small amount of specimen by using a form of the sample device having no absorbent filter or collecting surfaces. The sample thus collected accurately represents the concentration and composition of the liquid present in the native specimen, in that it retains higher molecular weight species which are frequently lost due to chromatographic effects in low volume filtrations. Liquid is drained from a volume of semi-solid specimen defined by the geometry of a collection space. The liquid drains through a filtering screen of non-absorbing porous material, and onto the liquid collecting surface of a detachable strip. The drained specimen is retained on the filter screen by adherence thereto and by self-adherence and viscosity.

A liquid sample is collected from a semi-solid specimen in the device 2 by opening the front panel 10 to expose the specimen receiving panel 14, and applying the specimen to the open specimen areas 20 at a uniform depth to fill the filter screen 30 within, using an implement such as a spatula, flat stick or small spoon. Excess specimen is wiped from all areas of the specimen receiving panel 14 except the open specimen areas 20. After the specimen is applied, that area of the liquid sample collecting panel 16 underlying the open specimen area 20 becomes wetted by liquid seeping through the porous filter screen 30. Particles smaller than the pores of the porous filter screen 30 may also be transferred to the sample collecting panel 16.

Modifications of the sampling device 2 that provide various degrees of separation of solid and liquid components can be provided by adjustments in the porosity of the filter screen 30. In addition, the filter screen 30 may be coated with a release agent, to decrease the likelihood that sample collection area 38 of the sample sticks will adhere to the screen.

The release agent can be selected from any of various suitable materials. Polyhydroxy compounds seem to be particularly suitable; however, water soluble polymers and fatty materials, such as liquid fatty acids and triglycerides, also were found to be effective. Polyhydroxy compounds are well known and an exhaustive list can readily be generated by those of skill in the art. These materials include, but are not limited to, various sugars, including pentoses and hexoses, polymers of alcohols, lecithin, alkylene glycols, and the like. While some release agents functioned more effectively than others, almost any (preferably liquid) material that can impregnate and/or coat the fibers of the filter screen 30 can be used to advantage in the invention.

For example, the following solutions were tested: 0.5%-1% polyvinylpyrrolidone (PVP—Calbiochem Corp., La Jolla, Calif.); 0.25%-1% polyethylene glycol (PEG—J. T. Baker, Jackson, Tenn.); 0.1%-1% Tween 20 (Sigma, St. Louis, Mo.); PAM ® cooking spray (an aerosol of partially hydrogenated vegetable (soy) oil and lecithin, described in U.S. Pat. No. 4,188,412)(Boyle-Midway, Inc., N.Y., N.Y.); and 6.25%-100% sucrose (Sigma, St. Louis, Mo.).

The coated screens were compared with non-coated filter screen in preventing sticking of the screen to the sample collecting portion 16 immediately and 45 minutes after smearing fecal samples. The filter screens coated 0.5% PEG, 0.25% PEG, 1% PEG, 1% PVP, 12.5% sucrose and PAM ® appeared to be better at preventing stickiness than the non-coated filter screen. The best solutions for preventing stickiness were 0.5% PEG and PAM ®, but PAM ® was difficult to work with. The Tween 20 solutions significantly increased the stickiness of the filter screens compared with non-coated screens.

We also tested the effects of 0.5% PEG and 12.5% sucrose for interference, sensitivity and stability in running a hemoglobin (Hb) test. Several non-coated, 12.5% sucrose, and 0.5% PEG coated filter screens fecal sample packets were smeared with either a negative fecal sample or a spiked fecal sample (2 mg Hb/g sample). Three packets from each group were allowed to dry for 45 minutes, 24 hours, and one week, respectively, before testing. They were either kept at 4° C., room temperature, 37° C., or 45° C. Upon running the Hb test on the packets, 0.5% PEG and 12.5% sucrose did not interfere with the test. There were no false positives or false negatives, and they appeared to be just as sensitive as the packets tested with non-coated filter screen stored at the same temperature.

The sampling device 2 may also be used to collect an undefined sample volume of intact specimen, whether liquid or semi-solid, according to embodiments that eliminate the filter screen 30. In these embodiments, the specimen may be sampled by direct application to the sample collecting portion 16 of the device or specifically to the sample area 38 of the transferring sticks 24 in any of their various attachments. This may be done according to several arrangements. First, the device may be made up with the bilayer 48 central leaflet of the preferred embodiment, but without the filter screen 30. In this configuration, the specimen can be applied directly to the sample collecting portion 16 through the open specimen application areas 20. Secondly, the device may be manufactured with a monolayer central leaflet comprising identically the specimen receiving portion 14 and the sample collecting portion 16, and the specimen applied directly thereon. Alternatively, the device may be manufactured without a central leaflet, wherein the inner surface of the back panel 12 may serve as the specimen receiving portion 14 or the sample collecting portion 16.

Other arrangements can be developed that conform to the general requirements of the invention, and retain the features of the preferred embodiment.

The sampling device 2 may be manufactured from various materials, such a cellulosic, paper or cardboard stock, plastic or plastic coated cellulose materials, or nitrocellulose, provided any such stock has enough rigidity to maintain the shape of the functional features. The material for the filter screen 30 should be non-absorbent or have a minimal absorbency. The material used for the filter screen 30 is of a uniform thickness so that together with the fixed open specimen areas 20, it defines a specimen volume when it is in place in the specimen application panel 14. In order to do this it should also have sufficient structural rigidity so that it retains a stable porosity when compressed by a specimen load. In a preferred embodiment, the filter screen 30 is of nylon mesh, and is preferably coated with a release agent.

The material used for the sample transferring sticks 24 need not be either absorbent or porous. Self-adherent biological specimens, for example, particularly those that are proteinaceous adhere to the surface of the transferring sticks 24. The liquid volumes which are collected on the sticks 24 is small in most applications and can adhere to the collecting surface by capillary action or as a moisture film. The liquid collecting capacity of the transferring sticks 24 can be conveniently expanded, when required, by an added layer of absorbent material on the surface of the liquid sample transferring sticks 24. The added layer may be a sheet of filter paper or particles of bibulous material, for example, cellulose flakes or dry Sepharose beads.

After the specimen is collected, the lower flap of the front panel 10 is inserted in the semi-circular slit 22 of the specimen receiving panel 14 so as to close the sampling device 2. The enclosed specimen may now be stored or transported in the device. The period the specimen can remain in the device and the conditions of storage are determined according to the stability of the analyte. The sampling device 2 can ultimately be conveniently discarded.

The collected sample is removed from the device 2 for analysis by means of the transferring sticks 24. To remove the sample according to the device of the preferred embodiment, one of the transferring sticks 24 integral to the sample collecting panel 16 is removed by means of an handle 40 provided by its distal end. The transferring sticks 24 are loosely held in the sample collecting panel 16 by attachments at the tip 36 and at points along the perforated edges 32. These attachments are easily torn by a slight pull on the handle 40. Thus, when the transferring stick 24 is grasped at its handle 40, it can be pulled free from the device 2. In other embodiments, wherein the transferring sticks 24 are attached to the interior side of the back panel 12 by an adhesive substance, they may be similarly pulled free.

The sample collecting area 38 of the transferring stick 24 retains a sample of either the intact specimen, which may contain solid particles, an intact liquid specimen, or a sample of liquid which has been drained from a semi-solid specimen. The sample is eluted from the transferring stick 24 by a volume of aqueous solution.

A sample which has been collected on the sample transferring stick 24 can be eluted for the determination of an analyte therein, or an analysis, for example a colorimetric determination, may be performed directly on the stick 24.

In a preferred embodiment of the invention, comprising a companion immunoassay procedure as described below, any solid particles present in the sample are filtered from the solution in the course of the assay procedure.

The sampling device 2 is conveniently incorporated into a kit, which also comprises materials and reagents for determining a particular analyte together with an elution cup or vessel which is conveniently used to transfer a collected liquid sample from the transferring sticks 24 of the sampling device 2 into a measured volume of liquid. The elution liquid may also be provided as a component of the kit.

In a preferred embodiment, the sampling device 2 is a component in a kit which provides a solid-phase enzyme immunoassay device together with accessory reagents for the immunological determination of hemoglobin. Two such devices are described in U.S. patent applications Ser. Nos. 06/909,020 and 07/189,049 both abandoned are conveniently adapted to the determination of hemoglobin in a liquid sample. These devices comprises a porous membrane which may have antibody to hemoglobin bound to its upper surface and which is fixed in a rigid housing. Absorbent material below the membrane acts to wick liquid away from the sample.

Any of the sample states discussed above, that is, a solid specimen or liquid drained from the specimen, may be analyzed for hemoglobin according to the procedure. A solid sample of the fecal specimen carried on the transferring stick is eluted using about 200 microliters of elution volume in the cup provided. A portion of the eluted semi-solid or liquid sample is then introduced into the assay device through a prefilter, which removes any particulate matter, and then onto the surface of the membrane. Any hemoglobin present in the sample is bound by the anti-hemoglobin antibodies of the membrane, while unbound substances pass through the membrane. The hemoglobin molecules thus bound to the surface of the membrane are then contacted with a volume of solution containing enzyme-labeled antihemoglobin antibodies and are bound also by these. Alternatively, the hemoglobin molecule may be bound initially by labeled anti-hemoglobin antibodies present in the elution liquid. When the enzyme thus bound to hemoglobin is allowed to react with a chromogenic substrate, the presence of color indicates the presence of hemoglobin. Control areas of the membrane are prepared with appropriate reagents to bind the detecting antibodies in the absence of hemoglobin (positive control) or to bind neither these antibodies nor the hemoglobin (negative control).

According to the preferred embodiment, the sampling device 2 is formed from a unitary blank 4 as best seen in FIGS. 5 and 6 and having a face surface 6 (FIG. 5) and a reverse surface 8 (FIG. 6). The blank comprises four panels in sequence: a front panel 10, a back panel 12, a specimen application panel 14 and a liquid sample collecting panel 16. The ends of adjoining panels are marked by fold line 42, lying between the sample collecting panel 16 and the specimen application panel 14, fold line 44, lying between the specimen application panel 14 and the back panel 12, and fold line 46 between the back panel 12 and the front panel 10. The face surface 6 of the blank 4 comprises those surfaces of the panels that face outwardly in the folded device 2; the reverse surface 8 comprises those surfaces of the panels that face inwardly in the folded device 2.

The sampling device 2 is formed by folding from the unitary blank 4. The sample collecting panel 16 is folded back along fold line 42 and against the specimen application panel 14 with their reverse surfaces 8 together, so that the sample transferring sticks 24 underlie the specimen application area 20. The back panel 12 is then folded along fold line 44 so that its reverse surface 8 is in contact with the face surface 6 of the sample collection panel 16. The front panel 10 is then folded along fold line 46 so that its reverse surface 8 is in contact with the face surface 6 of the specimen application panel 14. In this way, the specimen application panel 14 and the sample collection panel 16 form a sampling bilayer central leaflet 48 between the back panel 12 and the front panel 10.

The sampling device 2 may be used to collect samples from a variety of liquid or semi-solid specimens such as foods, soils, manufacturing wastes, or preferably biological samples. Appropriate semi-solid biological specimens are blood clots, sputum, mucous, pus, vomitus, gastric contents, wound debris, gross tissue from surgical specimens or biopsies, or fecal matter.

The collected liquid or semi-solid sample may be used to determine any substance or entity therein, any inorganic or organic chemical species, biological molecules such as enzymes, proteins, lipids or carbohydrates, infectious agents such as viruses, bacteria or parasites, cell types present in the specimen, or toxins.

Many other objects, features, and advantages of the present invention will be apparent to those of skill in the art.

Although the invention has been described in terms of certain preferred embodiments, it will be understood that the invention is intended only to be limited by the lawful scope of the claims that follow, and equivalents thereof.

What is claimed:

1. A sampling folder for use in the collection of a specimen, comprising:
a front panel,
a back panel,
a sample collecting panel at least partially covered by said front panel and having a specimen application area thereon, and
a specimen receiving panel covered by said sample collecting panel,
all of said panels being in overlying relationship, said front panel being openable to permit application of a specimen to said specimen application area;
said specimen receiving panel comprising, at least in part, a detachable sample transferring stick having a handle portion and a sample collecting portion,
said sample transferring stick positioned such that the sample collecting portion of said sample transferring stick is located underneath said specimen application area of said sample collecting panel and said handle portion is located under a part of said specimen receiving panel other than said specimen application area,
and wherein said back panel includes an opening therein through which said handle portion of said stick can be grasped and said stick can be removed.

2. The folder of claim 1, wherein said sample transferring stick is attached to the inside of said back panel.

3. The folder of claim 1, wherein said specimen receiving panel comprises a central leaflet between said front and back panels.

4. The system of claim 3, wherein said sample transferring stick is attached to the back of said central leaflet.

5. The folder of claim 1 or claim 3 further comprising a sheet of porous material in front of said specimen receiving panel, wherein said porous material is adapted to permit said specimen to be transferred through said porous material onto said specimen receiving panel.

6. The folder of claim 5 wherein said specimen application area is adapted to retain a defined volume of said specimen.

7. The folder of claim 5, wherein said porous material is coated with a release agent to prevent the porous material from sticking to said specimen receiving panel.

8. The folder of claim 7, wherein said release agent comprises a poly hydroxy compound.

9. The folder of claim 7, wherein said release agent comprises a sugar.

10. The folder of claim 7, wherein said release agent comprises polyethylene glycol.

11. The folder of claim 7, wherein said release agent comprises polyvinylpyrrolidone.

12. The folder of claim 1, additionally comprising indicia imprinted on said specimen application area, wherein said indicia are obscured when an adequate amount of sample is applied.

13. The folder of claim 1, wherein said back panel includes an opening therein through which said sample transferring stick can be removed.

14. The folder of claim 1, wherein said panels and said transferring stick are formed from cellulosic material.

15. The folder of claim 1, further comprising a layer of absorbent material on the sample collecting portion of said transferring stick.

16. The folder of claim 1, wherein said sample transferring stick is capable of transferring a semi-solid specimen.

17. The folder of claim 1 wherein said sample transferring stick is non-absorbent.

18. An assay system for determining the presence or quantity of an analyte, said system being in the form of a kit, said system comprising:
the folder of claim 1;
a mixing cup;
a liquid for use in said mixing cup to extract sample from said sample collecting portion; and
an assay device for determining the presence or quantity of an analyte in said extracted sample.

19. The system of claim 18, wherein said specimen is a stool sample and said analyte is hemoglobin.

20. The system of claim 18, wherein said assay device comprises an enzyme immunoassay.

21. A method for collecting a clinical specimen, using a sample collecting folder having a front panel, a back panel, a specimen receiving portion, and a detachable sample transferring stick, comprising the following steps in order:
opening the sample collecting folder by lifting the front panel to expose a specimen receiving area;
applying a clinical specimen which contains an analyte to said receiving area;
transferring said specimen to a sample collecting portion of said sample transferring stick;
closing said sample collecting folder by lowering said front panel; and
removing a sample transferring stick of said folder by grasping the handle portion thereof, said transferring stick containing a portion of said applied specimen adhering thereto, so that contact between a user and the specimen is avoided during the removal step.

22. The method of claim 21 where said specimen is a biological specimen.

23. The method of claim 21, wherein said specimen is a stool sample and said analyte is hemoglobin.

24. The method of claim 21, wherein said folder further comprises a sheet of porous material in front of said specimen collecting portion to which said specimen can be applied, wherein said porous material is adapted to permit only a portion of said specimen to be transferred through said porous material onto said specimen collecting portion.

25. The method of claim 21 further comprising analyzing the specimen adhering to said sample collecting portion of said sample transferring stick for the presence or quantity of an analyte.

26. The method of claim 25, wherein said analyzing step comprises an immunoassay.

27. The method of claim 21, wherein the said specimen is semi-solid.

28. A sampling folder for use in the collection of a specimen, comprising:
a front panel;
a back panel;
a sample collecting panel at least partially covered by said front panel and having a specimen application area thereon; and
a specimen receiving panel covered by said sample collecting panel; all of said panels being in overlying relationship, said front panel being openable to permit application of a specimen to said specimen application area,
said specimen receiving panel comprising a detachable sample transferring stick having a handle portion and a sample collecting portion, said sample collecting portion being of a material that does not absorb substantial amounts of fluid,
said sample transferring stick positioned such that the sample collecting portion of said sample transferring stick is located underneath said specimen application area of said specimen receiving panel and said handle portion is located under a portion of said specimen receiving panel other than said specimen application area.

29. The folder of claim 28 wherein said sample transferring stick additionally comprises an absorbent material, said absorbent material overlaying said sample collection portion.

* * * * *